United States Patent [19]
Florio

[11] Patent Number: 6,136,795
[45] Date of Patent: *Oct. 24, 2000

[54] DIETARY REGIMEN OF NUTRITIONAL SUPPLEMENTS FOR RELIEF OF SYMPTOMS OF ARTHRITIS

[75] Inventor: Vito V. Florio, Tamarac, Fla.

[73] Assignee: Omni Nutraceuticals, Inc, Los Angeles, Calif.

[ * ] Notice: This patent is subject to a terminal disclaimer.

[21] Appl. No.: 09/193,474

[22] Filed: Nov. 18, 1998

Related U.S. Application Data

[63] Continuation of application No. 08/952,272, filed as application No. PCT/US95/16722, Dec. 11, 1995, Pat. No. 5,840,715.

[51] Int. Cl.⁷ .......................... A61K 31/70; A61K 65/60; A61K 35/78
[52] U.S. Cl. ............................. 514/62; 514/54; 514/560; 514/825; 424/523; 424/195.1
[58] Field of Search ................ 514/54, 62, 560, 514/825; 424/523, 195.1

[56] References Cited

U.S. PATENT DOCUMENTS

| | | | |
|---|---|---|---|
| 3,683,076 | 8/1972 | Rovati | 514/62 |
| 4,843,095 | 6/1989 | Rubin | 514/558 |
| 5,166,048 | 11/1992 | Soll et al. | 435/1.1 |
| 5,364,845 | 11/1994 | Henderson | 514/54 |

FOREIGN PATENT DOCUMENTS

| | | |
|---|---|---|
| 0609001 | 8/1994 | European Pat. Off. . |
| 2223943 | 4/1990 | Germany . |

OTHER PUBLICATIONS

Life Extension Update, vol. 7, No. 3, Mar. 1994, The Life Extension Foundation, Hollywood FL.

Passwater, "Fish Oil Update" Keats Publishing Inc., New Canaan CT, 1987 (no month given).

Kurtzweil "Daily Values'Encourage Healthy Diet", in FDA Consumer Special Issue, May 1993; http://www.fda.gov/fdac/special/foodlabel accessed on Jun. 30, 1998.

*Primary Examiner*—Kathleen K. Fonda

[57] ABSTRACT

This invention is directed to a dietary regimen and a unique combination of nutritional supplements and a method. More specifically, this invention is directed to a unique combination of nutritional supplements which provides symptomatic relief from arthritis. The unique combination of nutritional supplements of this invention is believed to function by both increasing the available (effective blood level) of anti-inflammatory agents and promotion of the healing/regenerative process in the effected joints, thus, producing unexpected and lasting symptomatic relief from the debilitating effects of both osteoarthritis and rheumatoid arthritis. The essential nutritional supplements of the dietary regimen of this invention are as follows:

(a) gamma linolenic acid (unrefined), hereinafter "GLA"
(b) a mixture of eicosapentaenoic acid and docosahexaneoic acid, hereinafter collectively "EPA"
(c) a mixture of chondroitin sulfate, N-acetyl glucosamine sulfate, glucosamine sulfate and manganese aspartate, hereinafter collectively "CHONDROX"

The regimen is adjusted based upon the weight of the individual, and once symptomatic relief is achieved, the individual remains essentially free from the debilitating effects of arthritis so as long the daily regimen is faithfully followed.

4 Claims, No Drawings

DIETARY REGIMEN OF NUTRITIONAL SUPPLEMENTS FOR RELIEF OF SYMPTOMS OF ARTHRITIS

This application is a continuation of U.S. Ser. No. 08/952,272, filed Jan. 6, 1998, now U.S. Pat. No. 5,840,715 (issued Nov. 24, 1998), which is the U.S. National Stage Entry under 35 USC § 371 of international application PCT/US95/16722, filed Dec. 11, 1995.

BACKGROUND OF THE INVENTION

1. Field of the Invention

This invention is directed to a unique combination of nutritional supplements and a method. More specifically, this invention is directed to a unique combination of nutritional supplements which provides symptomatic relief from arthritis. The unique combination of nutritional supplements of this invention is believed to function by increasing the available (effective blood level) of anti-inflammatory agents and, thus, unexpected and lasting symptomatic relief from the debilitating effects of both osteoarthritis and rheumatoid arthritis.

2. Description of the Prior Art

Osteoarthritis or degenerative joint disease is the most common form of arthritis. It is seen primarily, but not exclusively, in the elderly; surveys have indicated that 80% of persons over the age of 50 have osteoarthritis. Under the age of 45, osteoarthritis is much more common in men; after age 45 it is ten times more common in women than men.

The weight-bearing joints and joints of the hands are the joints principally affected by the degenerative changes associated with osteoarthritis. Specifically, there is much cartilage destruction, followed by hardening, and the formation of large bone spurs (Calcified osteophytes) in the joint margins. Pain, deformity and limitation of motion in the joint results. Inflammation is usually minimal.

Osteoarthritis is divided into two categories, primary and secondary osteoarthritis. In primary osteoarthritis, the degenerative wear-and-tear process occurs after the fifth and sixth decades, with no predisposing abnormality apparent. The cumulative effects of decades of use leads to the degenerative changes by stressing the integrity of the collagen matrix of the cartilage. Damage to the cartilage results in the release of enzymes that destroy collagen components. With aging, there is a decreased ability to restore and synthesize normal collagen structures.

Secondary osteoarthritis is associated with some predisposing factor responsible for the degenerative changes. Various predisposing factors in secondary osteoarthritis include congenital abnormalities in joint structure or function (e.g. excessive joint mobility and abnormally shaped joint surfaces), trauma (obesity, fractures along joint surfaces, surgery, etc.) crystal deposition, presence of abnormal cartilage, and previous inflammatory disease of joint (rheumatoid arthritis, gout, septic arthritis, etc.).

The causes of osteoarthritis are, thus, believed to include one or more of the following conditions or imbalances in the body's chemistry:

Excessive mobility/joint instability.

Age-related changes in collagen matrix repair mechanisms.

Hormonal and sex factors.

Altered biochemistry.

Genetic predisposition.

Inflammation.

Fractures and mechanical damage.

Inflammatory joint disease.

Others.

As anyone who has been afflicted by this disease can attest, the onset of osteoarthritis can be very subtle, morning joint stiffness often being the first symptom. As the disease progresses, there is pain on motion of the involved joint, that is made worse by prolonged activity and relieved by rest. There are usually no signs of inflammation.

The specific clinical picture varies with the joint involved. Disease of the hands leads to pain and limitation of use. Knee involvement produces pain, swelling and instability. Osteoarthritis of the hip causes local pain and a limp. Spinal osteoarthritis is very common and may result in compression of nerves and blood vessels, causing pain and vascular insufficiency.

The classic presentation of osteoarthritis is easy to distinguish from other types of arthritis, especially rheumatoid arthritis, which is usually associated with much more inflammation of surrounding soft tissues.

The data collected from the earliest signs of osteoarthritis to the most advanced stages suggest that cellular and tissue response to osteoarthritis (OA) is purposeful and is aimed at repair of the damaged joint structure; and, that the process contributing to OA thus appears to be able to be arrested and sometimes reversed. Accordingly, the major therapeutic goal appears to be enhancing repair processes by various connective tissue cells.

Several studies have attempted to determine the "natural course" of OA. In one case study the natural course of OA of the hip was studied over a ten-year period. All subjects had changes suggestive of advanced osteoarthritis, yet the researchers reported marked clinical improvement and radiological recovery of the joint space in 14 of 31 hips. The authors purposely applied no therapy and regarded their results as reflecting the natural course of the disease.

These results as well as others raise some interesting questions. Does medical intervention in some way promote disease progression? Can various natural therapies enhance the body's own response towards health? The answer to both of these questions appears to be yes.

Medication & Side Effects

The first drug generally employed in the treatment of osteoarthritis is aspirin. It is often quite effective in relieving both the pain and inflammation. It is also relatively inexpensive. However, since the therapeutic dose required is relatively high (2 to 4 grams per day), toxicity often occurs. Tinnitus (ringing in the ears) and gastric irritation are early manifestations of toxicity.

Other non-steroidal anti-inflammatory drugs (NSAIDs) are often used as well, especially when aspirin is in ineffective or intolerable—ibuprofen (Brufen, Motrin), fenoprofen (Fenopron), indomethacin (Indocid), naproxen (Naprosyn), tolmetin (Tolectrin) and sulindac (Clinoril). These drugs are also associated with side effects including gastrointestinal upset, headaches and dizziness, and are therefore recommended for only short periods of time.

One side effect of aspirin and other NSAIDs that is often not mentioned is their inhibition of cartilage repair (i.e. inhibition of collagen matrix synthesis) and acceleration of cartilage destruction in experimental studies. Since osteoarthritis is caused by a degeneration of cartilage it appears that, while NSAIDs are fairly effective in suppressing the symptoms, they possibly worsen the condition by inhibiting cartilage formation and accelerating cartilage destruction. This adverse effect of NSAID therapy has been upheld in studies which have shown that NSAIDs use is associated with acceleration of osteoarthritis and increased joint destruction. Simply stated, NSAIDs appear to suppress the symptoms but accelerate the progression of osteoarthritis.

Dietary Regimen Effect on Disease

Alternatives to medication include a dietary regimen which may exclude the consumption of some foods and/or the use of certain nutritional supplements. Primary dietary therapy involves the achievement of normal body weight; excess weight means increased stress on weighit-bearing joints affected with osteoarthritis. A general healthy diet rich in complex carbohydrate and dietary fiber is recommended.

Childers, a horticulturist, popularized a diet in the treatment of osteoarthritis that eliminated foods from the genus solanaceae (nightshade family) after finding this simple dietary elimination cured his osteoarthritis. Childers developed a theory that genetically susceptible individuals might develop arthritis, as well as a variety of other complaints, from long-term low level consumption of solanum alkaloids that are found in tomatoes, potatoes, eggplant, peppers and tobacco. Presumably these alkaloids inhibit normal collagen repair in the joints or promote the inflammatory degeneration of the joint. Although remaining to be proved, this diet may offer some benefit to certain individuals.

It has and continues to be increasingly accepted that nutritional considerations, specifically, the consumption of nutritional supplements, can control and reverse the pain and crippling effects of arthritis. The following is representative of some of the more credible clinical investigation with respect to certain nutritional supplements.

Niacinamide—Dr. William Kaufman has reported very good clinical results in the treatment of hundreds of patients with rheumatoid and osteoarthritis using high dose niacinamide (i.e. 900 mcg to 4 g in divided dose daily). Niacinamide at this high dose can result in significant side effects (glucose intolerance, liver damage) and should therefore be instituted under strict medical supervision.

Methionine—The essential amino acid methionine, administered as S-adenosyl-methionine, was shown to be superior to ibuprofen (Motrin) in the treatment osteoarthritis in a double-blind clinical trial. The positive effect in this trial is consistent with several other clinical studies. Methionine is a sulfur-containing amino acid which is very important in cartilage structures, especially proteoglycans and glycosaminoglycans, Glycosaminoglycans—Injectable glycosaminoglycan polysulphate and activated acid-pepsin-digested calf tracheal cartilage as well as other glycosaminoglycan preparations have yielded positive results in controlled trials and experimental studies. Results seem to indicate these compounds may address some of the underlying causes of the degenerative process characteristic of osteoarthritis.

It must be pointed out that these latter studies have all utilized injectable formulas. It is highly unlikely similar results could be obtained with these formulations when administered orally as intestinal absorption of glycosaminoglycans having a molecular weight greater than 4,000 is quite poor without the aid of special vehicles, such as liposomes, or possible enteric-coating.

Many commercial products are available that contain chondroitin sulfate (molecular weight 30,000). It must be pointed out the majority of these formulas are probably of no greater benefit than placebo as chondroitin sulfate is not absorbed to any significant degree. Enteric locating or administering in the form of a liposome may increase bio-availability but this has yet to be fully determined. In addition, it is possible that smaller fragments of the molecule may have some therapeutic effect, but again this has yet to be determined.

Superoxide Dismutase—Like glycosaminoglycan preparations, intra-articular injection of superoxide dismutase (SOD) has demonstrated significant therapeutic effects in the treatment of OA. Whether oral SOD preparations are absorbed orally has yet to be determined. Preliminary indications are that it is probably not.

Vitamin E—A clinical trial using 600 iu of vitamin E in patients with osteoarthritis demonstrated significant benefit from the vitamin E. The benefit was thought to be due to vitamin E's antioxidant and membrane stabilizing actions. Later studies have shown that vitamin E has an ability to inhibit the enzymatic breakdown of cartilage as well as stimulate cartilage synthesis.

Vitamin C—Deficient vitamin C intake is common in the elderly, resulting in altered collagen synthesis and compromised connective tissue repair. Several studies have demonstrated that vitamin C has a positive effect on cartilage, and one confirmed the importance, indeed necessity, for an excess of ascorbic acid in human chondrocyte protein synthesis. In a study of experimental OA in guinea pigs cartilage erosion was found to be much less and the overall changes in and around the OA joint milder in animals kept on high doses of vitamin C.

Vitamin C and E appear to possess synergistic effects. Thus, both vitamins E and C appear to enhance the stability of sulfated proteoglycans in the complex structure comprising articular cartilage. Judicious use of these vitamins in the treatment of osteoarthritis, either alone or in combination with other therapeutic means, may thus be of great benefit to the patient population by retarding the erosion of cartilage.

Pantothenic Acid—Acute deficiency of pantothenic acid in the rat causes a pronounced failure of cartilage growth and eventually produces similar lesions to osteoartbritis. This implicates low pantothenic acid levels in the development of human OA. Clinical improvements in OA symptomatology has been reported with the daily supplementation of 12.5 mg pantothenic acid, although such results often took 7–14 days before manifesting. (A larger double-blind study in patients with primarily rheumatoid arthritis displayed no significant benefit with 500 mg pantothenic acid administration.)

Vitamins A, B6 and E, Zinc and Copper—These nutrients are required for the synthesis of normal collagen and maintenance of cartilage structures. A deficiency of any one of these would allow accelerated joint degeneration.

Physical Therapy

Various physical therapies (exercise, heat, cold, diathermy, ultrasound, etc.) are often very beneficial in improving joint mobility and reducing pain in sufferers of OA. The importance of physical therapy appears to be quite significant, especially when administered regularly. Much of the benefit of physical therapy is thought to be a result of achieving a proper water content within the joint capsule.

Clinical and experimental studies seem to indicate short-wave diathermy may be of the greatest benefit. Combining short-wave diathermy therapy with periodic ice massage, rest and appropriate exercises appears to be the most sensible approach. Proper exercises include isometric exercises and swimming; these types of exercises increase circulation to the joint and strengthen surrounding muscles without placing too much strain on the joint.

In summary, the cause, progression and treatment of the disease presents a complex and has up to now generally required a multi-phasic approach to proper treatment. More specifically, to the extent that consumption of certain foods is believed to influence the progression of the disease, all simple, processed and concentrated carbohydrates must be avoided. In addition, complex-carbohydrate, high-fiber foods should be stressed and fats should be kept to a minimum. Moreover, plants of the solanaceae family should be eliminated (tomatoes, potatoes, eggplant, peppers and tobacco).

Where the disease is influenced by the consumption of dietary supplements, one or more of the supplements discussed above are available as an option, however, medical supervision is generally recommended. In addition, daily exercises including isometric exercises and swimming short-wave diathermy and other physical therapy treatments may be helpful.

As is evident from the foregoing, the treatment of OA involves both the abatement of the pain associated with the disease and the fostering of healing of the effected tissues. The use of the common analgesics (e.g. aspirin, ibuprofen, etc.) while relieving the pain may in fact accelerate the progression of the disease by inhibition of the healing processes associated with cartilage repair. Moreover, the attempts to treat the disease by the focusing upon a single natural occurring compound, or limited number of compounds, has generally resulted in only limited and short term improvements. Accordingly, there continues to be a need for a safe and effective regimen for the treatment of OA but yet is affordable and does not require the supervision of a medical professional.

OBJECTS OF THE INVENTION

It is the object of this invention to remedy the above as well as related deficiencies in the prior art.

More specifically, it is the principle object of this invention to provide a unique combination of nutritional supplements in effective amounts, taken in a prescribed sequence, which is both safe and effective to relieve the debilitating symptom of arthritis.

It is another object of this invention to provide a unique combination of nutritional supplements in effective amounts, taken in a prescribed sequence, which apparently permits extended relief from lower dosage of these agents.

It is still yet another object of this invention to provide a unique combination of nutritional supplements in effective amounts, taken in a prescribed sequence which is easily digestible, thus, free from many of the side-effects associated with the more common anti-inflammatory medicines.

Additional objects include a method for the relief of symptoms of arthritis through the ingestion of effective amounts of readily digestible nutritional supplements.

SUMMARY OF THE INVENTION

The above and related objects are achieved by the provision of unique combination of nutritional supplements in effective amounts, taken in a prescribed sequence, to produce a readily ingestible formulation that relieves the symptomatic pain associated with the more common forms of arthritis.

In brief, this invention comprises a unique combination of nutritional supplements in effective amounts, taken in a prescribed sequence that reportedly have some demonstrated effectiveness in the treatment of the debilitating effects of arthritis, together a chondroitinsulfuric acid salt, (a constituent of healthy cartilage) to provide symptomatic relief from the pain associated with arthritis. The precise mechanism or physiology of action of the formulation on the afflicted individual is not known, nor the precise nature of the pain complex of this disease.

The following nutritional supplements, when taken in effective amounts and in the appropriate regimen provide both unexpected and lasting symptomatic relief from arthritis:

(a) gamma linolenic acid (unrefined), hereinafter "GLA"

(b) a mixture of eicosapentaenoic acid and docosahexaneoic acid, hereinafter "EPA"

(c) a mixture of chondroitin sulfate, N-acetyl glucosamine sulfate, glucosamine sulfate and manganese aspartate, hereinafter "CHONDROX"

Generally, the commercially available preparations of the foregoing essential supplements contain additional ingredients, e.g. vitamins such as Vitamin E and C, in relatively minor amounts. It is believed that these additional ingredients, where present, are not believed to contribute to the efficacy of the supplement formulation; and, are simply included for their anti-oxidant properties to enhance the shelf life of the commercial preparation.

It would appear that all of the above supplements are essential to complete pain relief, and that the gamma linolenic acid (GLA) is probably the principle ingredient is abating the symptomatic pain associated with the arthritic condition. Moreover, it also appears that the effectiveness of GLA is linked to the presence of EPA in the diet; and, that the dietary demands for EPA in the above regimen is a function of the individuals weight.

It is further hypothesized that the combination of anti-inflammatory dietary supplement with chondroitinsulfuric acid salt not only reduces the inflammation of the joint in the afflicted area and but also permits the healing of the damaged cartilage. The precise formulation is based upon body weight of the affected individual.

DESCRIPTION OF THE INVENTION INCLUDING PREFERRED EMBODIMENTS

The formulation of the invention includes a unique combination of nutritional supplements in effective amounts, taken in a prescribed sequence, to effectively relieve the debilitating symptomatic conditions associated with arthritis.

In general, the unique combination of nutritional supplements of this invention includes a number constituents which are reported as providing anti-inflammatory therapy, and yet individually and in the reported combinations fail to provide the dramatic and long term relief afforded with this invention. More specifically, the unique combination of nutritional supplements of this invention include:

(a) gamma linolenic acid (unrefined), hereinafter "GLA"

(b) a mixture of eicosapentaenoic acid and docosahexaneoic acid, hereinafter "EPA"

(c) a mixture of chondroitin sulfate, N-acetyl glucosamine sulfate, glucosamine sulfate and manganese aspartate, hereinafter "CHONDROX"

Gamma linolenic acid (GLA) is generally present in a number of natural sources, including specifically, from borage seed oil and other plant. There is some support in the literature that eicosapentaenoic acid is suitable in the treatment of rheumatoid arthritis Eicosapentaenoic acid and docosahexaneoic acid (collectively "EPA") is obtained from fish (e.g. sardines and mackerel). These constituents comprise highly unsaturated fatty acids, generally containing as many as five (5) unsaturated double bonds, and thus highly susceptible to oxidation. There is some support in the literature that eicosapentaenoic acid is efficacious in the treatment of rheumatoid arthritis.

Chondroitin sulfate is a high viscosity mucopolysaccharride with N-acetylchondrosine as a repeating unit and with one sulfate group per disaccharide unit. This compound can be prepared by any one of number of techniques disclosed in the technical literature (e.g. Schubert, *Fed. Proc.* 17, 1099 (1958)). This compound is generally found in the skeletal and soft connective tissue of the human body. There is some support in the literature that chondroitin sulfate is involved in the regeneration of cartilage and other connective tissues.

N-acetyl glucosamine sulfate and glucosamine sulfate are generally present in chitin, in mucoproteins and in mucopolysaccharides. There is some support in the literature that chondroitin sulfate is efficacious as an anti-arthritic. The N-acetyl glucosamine sulfate, glucosamine sulfate and chondroitin sulfate are taken together and thus collectively referred as "CHONDROX".

A dietary regimen which includes each of the foregoing supplements, taken at the prescribed intervals and in the appropriate amounts, both relieves the debilitating effects of arthritis in the short term, and is believed to promote healing of the tissues in the inflamed joints. The precise regimen, as empirically determined, is apparently dependent upon body weight, which appears to increase the body's requirements for GLA. This difference may also be gender dependent, women subjects generally weighing less than men in the test population for this therapy.

In one of the preferred embodiments of this invention, the following recommended regimen is both safe and effective for relief from the symptomatic effects of arthritis, without the attendant side effects generally associated with medication.

| Dosage* | Supplement | Time of Day |
|---|---|---|
| Individuals Weighing Less Than 150 pounds | | |
| 1 | CHONDROX | Morning |
| 1 | EPA | Morning |
| 1 | CHONDROX | PM |
| 1 | GLA | PM |

| Dosage | Supplement | Time of Day |
|---|---|---|
| Individuals Weighing More Than 150 pounds, but Less Than 200 pounds | | |
| 2 | CHONDROX | Morning |
| 1 | EPA | Morning |
| 1 | GLA | Morning |
| 1 | CHONDROX | Mid-Day |
| 1 | EPA | Mid-Day |
| 1 | CHONDROX | PM |
| 1 | GLA | PM |
| Individuals Weighing More Than 200 pounds | | |
| 2 | CHONDROX | Morning |
| 1 | BPA | Morning |
| 1 | GLA | Morning |
| 2 | CHONDROX | Mid-Day |
| 1 | EPA | Mid-Day |
| 1 | GLA | Mid-Day |
| 2 | CHONDROX | PM |
| 1 | EPA | PM |
| 1 | GLA | PM |

*The recommended dosage is preferably an amount which is in excess of the minimum daily requirements for an individuals body weight and metabolism; and, is preferably a multiple (2× or 3×) of such minimum daily requirements (MDR). Where no MDR is established for the supplement listed, the unit dosage should range from about 250 to 500 mg (alternatively, should parallel the dosage for the supplement that is taken at the same time period for which an MDR has been established).

As is evident from the foregoing, the body's demand for CHRONDOX requires that this supplement be taken a minimum of twice, and in heavier individuals, three times a day. The presence of EPA in the blood is known to inhibit the metabolism of the gamma linolenic acid (GLA), thus, EPA should be taken in the morning with the initial consumption of CHRONDOX.

When the above regimen is followed, the pain associated with arthritis will begin to subside within about one (1) to two (2) days thereafter; and, provides essentially continuous relief so long as the regimen is followed. Where the regimen is discontinued, the debilitating pain will return within a relatively brief period (4–6 days) In some instances, the therapeutic effects of the formulation provides pain relief for even a longer period (up to 14 days) after the regimen has been discontinued. Upon resumption of the regimen, the pain once again is abated, and no side effects are experienced even after several months of continuous use. Present experience indicates that essentially no adverse side effects have been experienced after a year of continuous use.

In an effort to determine which of the various constituents is most essential to pain relief, one component of the supplement regimen is discontinued, and the results observed. This process is repeated so as to obtain a degree of insight and correlation of a supplements role in the dietary regimen. It would appear that all of the above supplements are essential to complete pain relief, and that the gamma linolenic acid (GLA) is probably the principle ingredient in abating the symptomatic pain associated with the arthritic condition. Moreover, it also appears that the effectiveness of GLA is linked to the presence of EPA in the diet; and, that the dietary demands for EPA in the above regimen is a function of the individual's weight. The long term benefits of this regimen are apparently attributable to the effectiveness of the chondroitin sulfate and N-acetyl glucosamine sulfate which apparently results in reversal of the cartilage deterioration and, thus, stabilization and repair of the afflicted joint.

The foregoing supplements are available in a variety of convenient forms and dosage levels to accommodate the foregoing regimen. For example, chondroitin sulfate and N-acetyl glucosamine sulfate are available for the Prolongevity, Ltd. (The Life Extension Foundation) under the CHONDROX label—the typical capsule containing 250 mg each of N-acetyl glucosamine sulfate and glucosamine, and 100 mg chondroitin sulfate. Similarly, eicosapentaenoic acid and docosahexaneoic acid are available for the Prolongevity, Ltd. (The Life Extension Foundation) under the MEGA EPA label—the typical capsule containing 400 mg eicosapentaenoic acid, 300 mg docosahexaneoic acid, vitamin E (2 IU) and 2 mg vitamin C (both of such vitamins apparently being present for their anti-oxidant properties. Similarly, Gamma linolenic acid is available for the Prolongevity, Ltd. (The Life Extension Foundation) under the MEGA GLA label—the typical capsule containing 300 mg gamma linolenic acid.

In another of the preferred embodiments of this invention, the dietary supplements for a given time frame are incorporated into a unitary dose (in the form of, for example, capsules, tablets, or liquids), and taken in accordance with written and/or graphic label or package insert instructions.

The precise amount of the recommended supplement may have to be adjusted depending upon the severity of individual's condition and the extent of progression of the disease. Notwithstanding, once the progression of the disease has been arrested, the foregoing regimen is effective to maintain the individual's freedom from pain and further progression of the disease.

The foregoing description has been provided to illustrated one or more of the preferred embodiments of this invention and is not intended to delineate its scope which is set forth in the following claims.

What is claimed is:

1. A method for providing symptomatic relief from the debilitating effects of arthritis in a patient, comprising:
    A. providing for daily consumption by said patient of (a) from about, 250 to about 1500 mgs of a natural source of gamma linolenic acid, (b) from about 250 to about 1500 mgs of a natural source of omega-3 fatty acid selected from the group consisting of eicosapentaenoic acid, docosahexaenoic acid and mixtures thereof, and (c) from about 500 to about 3000 mgs of a mixture containing a natural source of glucosamine and a natural source of chondroitin or their corresponding salts; and
    B. maintaining said daily consumption as so to relieve the debilitating effects of arthritis,
    with the proviso that the mixture of subparagraph (c) and the omega-3 fatty acid(s) of subparagraph (b) be taken together at least once in the morning; and, that the mixture of subparagraph (c) and the natural source of gamma linolenic acid of subparagraph (a) be taken together in the evening.

2. An article of manufacture comprising:
    A. unit packages in the formn of capsules, tablets, or liquids comprising (a) from about, 250 to about 1500 mgs of a natural source of gamma linolenic acid, (b) from about 250 to about 1500 mgs of a natural source of omega-3 fatty acid selected from the group consisting of eicosapentaenoic acid, docosahexaenoic acid and mixtures thereof, and (c) from about 500 to about 3000 mgs of a mixture containing a natural source of glucosamine and a natural source of chondroitin or their corresponding salts; and
    B. written and/or graphic instructions indicating that the mixture of that the mixture of subparagraph (c) and the omega-3 fatty acid(s) of subparagraph (b) be taken together at least once in the morning; and, that the mixture of subparagraph (c) and the natural source of gamma linolenic acid of subparagraph (a) be taken together in the evening,
    said instructions further comprising a table indicating effective amounts for patients of different weights of each of the natural source of gamma linolenic acid of subparagraph (a), the omega-3 fatty acid(s) of subparagraph (b), and the mixture of subparagraph (c) to be consumed in accordance with a daily regimen for the symptomatic relief from debilitating effects of arthritis.

3. A method for providing symptomatic relief in an individual patient suffering from debilitating effects of arthritis, comprising:
    A. providing a dietary regimen comprising daily consumption of a combination of dietary supplements which includes (a) a pain relief effective amount of a natural source of gamma linolenic acid, (b) a natural source of an omega-3 fatty acid selected from the group consisting of eicosapentaenoic acid, docosahexaenoic acid, and mixtures thereof, wherein said omega-3 fatty acid is present in about an equal amount by weight relative to the gamma linolenic acid, and (c) a cartilage regeneration effective amount of a mixture containing a natural source of glucosamine and a natural source of chondroitin or their corresponding salts; and
    B. maintaining said daily consumption as so to relieve the debilitating effects of arthritis,
    with the proviso that the mixture of subparagraph (c) and the omega-3 fatty acid(s) of subparagraph (b) be taken together at least once in the morning; and, that the mixture of subparagraph (c) and the natural source of gamma linolenic acid of subparagraph (a) be taken together in the evening.

4. The method of claim 3, wherein said daily consumption is adjusted once an idividual's pain has been arrested to maintain said individual's freedom from pain and limit further progression of said arthritis.

* * * * *